(12) United States Patent
Tran (10) Patent No.: US 9,072,600 B2
(45) Date of Patent: Jul. 7, 2015

(54) CURVATURE CHANGING ACCOMMODATIVE INTRAOCULAR LENS

(71) Applicant: NOVARTIS AG, Basel (CH)

(72) Inventor: Son Trung Tran, Arlington, TX (US)

(73) Assignee: NOVARTIS AG, Basel (CH)

( * ) Notice: Subject to any disclaimer, the term of this patent is extended or adjusted under 35 U.S.C. 154(b) by 56 days.

(21) Appl. No.: 14/095,537

(22) Filed: Dec. 3, 2013

(65) Prior Publication Data
US 2014/0180404 A1    Jun. 26, 2014

Related U.S. Application Data

(60) Provisional application No. 61/740,583, filed on Dec. 21, 2012.

(51) Int. Cl.
*A61F 2/16* (2006.01)

(52) U.S. Cl.
CPC .............. *A61F 2/1635* (2013.01); *A61F 2/1648* (2013.01); *A61F 2002/1681* (2013.01)

(58) Field of Classification Search
CPC .............................. A61F 2/1635; A61F 2/1648
USPC .............. 623/6.13, 6.34, 6.37, 6.38, 6.4, 6.43
See application file for complete search history.

(56) References Cited

U.S. PATENT DOCUMENTS

| 2008/0161913 A1 | 7/2008 | Brady et al. |
| 2009/0204210 A1 | 8/2009 | Pynson |
| 2012/0310345 A1 | 12/2012 | Olcina Portilla |

FOREIGN PATENT DOCUMENTS

WO    WO 2006103674 A2  *  10/2006

OTHER PUBLICATIONS

PCT/US2013/072854, International Search Report and Written Opinion, International Searching Authority, Dec. 3, 2013, 8 pgs.

* cited by examiner

*Primary Examiner* — David H Willse
*Assistant Examiner* — Javier Blanco
(74) *Attorney, Agent, or Firm* — Jason Finch (57) ABSTRACT

A curvature changing accommodative intraocular lens for implantation into the eye of a patient includes a lens body having a base lens which has a base lens power, and a haptic structure including haptic elements projecting from the base lens. An actuator is placed into engagement with the lens body, and includes actuator haptic elements. At least one fluidic optical element is received between the actuator and base lens of the lens body and contains a fluid material therein. During accommodation of the patient's eye, the haptic elements of the lens body and actuator are engaged and apply a force to the fluidic optical element, causing the fluidic optical element to be deformed to generate an additional lens power to adjust the patient's vision.

3 Claims, 8 Drawing Sheets

CURVATURE CHANGING ACCOMMODATIVE INTRAOCULAR LENS

This application claims the priority of U.S. Provisional Patent Application No. 61/740,583 filed Dec. 21, 2012.

FIELD OF THE INVENTION

The present invention relates generally to intraocular lenses (IOLs), and particularly to curvature changing accommodative IOLs including selectable and replaceable curvature changing elements for correction of a patient's vision.

BACKGROUND OF THE INVENTION

Intraocular lenses (IOLs) typically are implanted within a patient's eye during cataract surgery when the natural crystalline lens of the patient's eye has become clouded due to formation of cataracts, or is otherwise in need of replacement to compensate for lost optical power of the natural lens. In the past, such IOLs have included monofocal IOLs in which light from distant objects is focused onto the retina to improve distance vision (although for nearer objects, patients implanted with such monofocal IOLs often still have to use reading glasses for correction of vision for close up or nearer objects), and more recently accommodating IOLs have been developed, which are designed to adjust the patient's vision in response to natural accommodative forces resulting from the contraction and expansion of the muscles of the ciliary body of the patient's eye. However, it has been difficult to provide consistent continued accommodation of such IOLs over time, especially in patients with astigmatism. As the capsular bag regrows and "shrink wraps" the IOL, the accommodative forces applied to the IOL can become lessened, thus reducing the effectiveness of the IOL in correcting the vision of the patient. It is also often difficult to ensure consistent and accurate placement of such IOLs, especially with unknown capsular bag and/or capsulorhexis sizes. Other types of IOLs further have been developed including haptic elements that can engage or be implanted into ciliary body portions of the patient's eye.

Accordingly, it can be seen that a need exists for an enhanced accommodative IOL that addresses the foregoing and other related and unrelated problems in the art.

SUMMARY OF THE INVENTION

Briefly described, the present invention generally relates to intraocular lenses and in particular to curvature changing accommodative intraocular lenses (IOLs) designed to help restore presbyopic vision to patients. For example, in one embodiment, the accommodative IOL according to the principles of the present invention can be used for correction of cataracts in patients, with the accommodative IOL generally being implanted within the capsulor bag of the patient's eye as a replacement for the natural crystalline lens of the patient's eye. The accommodative IOL according to the principles of the present invention further is designed to provide for substantially continued accommodation with an accommodative amplitude of upwards of two diopters or greater and can include a lens component for correction of residual refractive error or astigmatism of the patient's eye.

According to one embodiment, the accommodative IOL generally can include a lens body including a base lens having a base lens power such as for correction of residual refractive error or astigmatism, and a haptic structure extending from a peripheral side edge of the base lens. The haptic structure can include a series of radially projecting lens haptic elements, with an outer, peripheral connecting ring extending therebetween and being spaced from the peripheral side edge of the base lens. An actuator further can be attached to the lens body, with the actuator being received over the centrally located base lens portion of the lens body. The actuator can include a substantially ring-shaped body having a central opening generally aligned with the base lens of the lens body, and a series of radially projecting actuator haptic elements. The actuator haptic elements further can include a substantially U-shaped structure, each having a curved body with locking members or catch portions formed at distal ends thereof. The locking members or catch portions of the actuator haptic elements can be received about and engage the outer connecting ring of the lens body so as to connect the actuator and lens body, defining a substantially unitary IOL having a cross-haptic structure.

At least one fluidic optical element generally will be received between the ring-shaped body of the actuator and the central base lens portion of the lens body. The at least one fluidic optical element generally can comprise a membrane or bag formed from a flexible, soft biocompatible material, such as a soft acrylic, silicone or hydrogel optic material. The membrane or bag of the fluidic optical element also generally will be filled with an aqueous fluid material such as a liquid, gel or compressible solid material, and in an installed, uncompressed state can have a reduced or null/zero lens power.

When implanted within the capsular bag of the patient's eye, the accommodating IOL will be in a generally unaccommodated or disaccommodated state with the fluidic optical element being in a substantially flattened configuration between the actuator and base lens of the lens body. As the muscles of the ciliary body of the patient's eye are moved during accommodation, the cross-action haptic structure of the IOL will be engaged, causing the actuator and lens body to move closer together, creating a ring pressure so as to apply a corresponding axial compressive force to the fluidic optical element along the edges thereof. This axial compressive force can cause the fluid within the fluidic optical element to be urged toward a center lens portion thereof, causing the center lens portion of the membrane or bag to expand or bulge outwardly to change the curvature of the fluidic element and thus generate a lens or optic power in addition to the base power of the base lens of the lens body. Thereafter, as the muscles of the ciliary body of the patient's eye relax and contract during disaccommodation, the axial compressive force acting on the cross-action haptic structure of the IOL from accommodation is reduced, enabling the resilient cross-haptic structure to expand outwardly and the fluidic optical element to return to a substantially flattened, unaccommodated configuration to enable the patient's eye to focus more clearly on distant objects.

Various objects, features and advantages of the curvature changing accommodative IOL according to the principles of the present invention will become apparent to those skilled in the art upon a review of the following detailed description, when taken in conjunction with the accompanying drawings.

Those skilled in the art will appreciate and understand that, according to common practice, the various features of the drawings discussed below are not necessarily drawn to scale, and that dimensions of various features and elements of the drawings may be expanded or reduced to more clearly illustrate the embodiments of the present invention described herein.

DETAILED DESCRIPTION

Referring now in greater detail to the drawings in which like numerals indicate like parts throughout the several views, FIGS. 1A-3 generally illustrate one embodiment of a curvature changing accommodative intraocular lens (IOL) and components thereof according to the principles of the present invention. The IOL 10 of the present invention generally can be implanted into the eye of a patient for correction of visual deficiencies of the patient's eye due to cataracts and/or residual refractive errors or astigmatism for enabling correction of the patient's vision in response to the natural accommodative operation and function of the patient's eye. As indicated in FIGS. 4A-4B, the IOL 10 generally can be implanted within the capsular bag C of the patient's eye, so as to be engaged by the capsular bag during accommodating and disaccommodating movements or operations of the patient's eye. The position or location of the implanted IOL further can be varied as needed, as will be understood by those skilled in the art. The IOL 10 of the present invention is adapted to provide substantially consistent, continued accommodated visual adjustment for the patient's eye and can be implanted in varying or unknown size capsular bags and/or capsular-hexis sizes while working with the natural accommodative movement and stimuli of the patient's eye for providing desired correction of the patient's vision for viewing distant or more close-up objects.

Figure 1A:
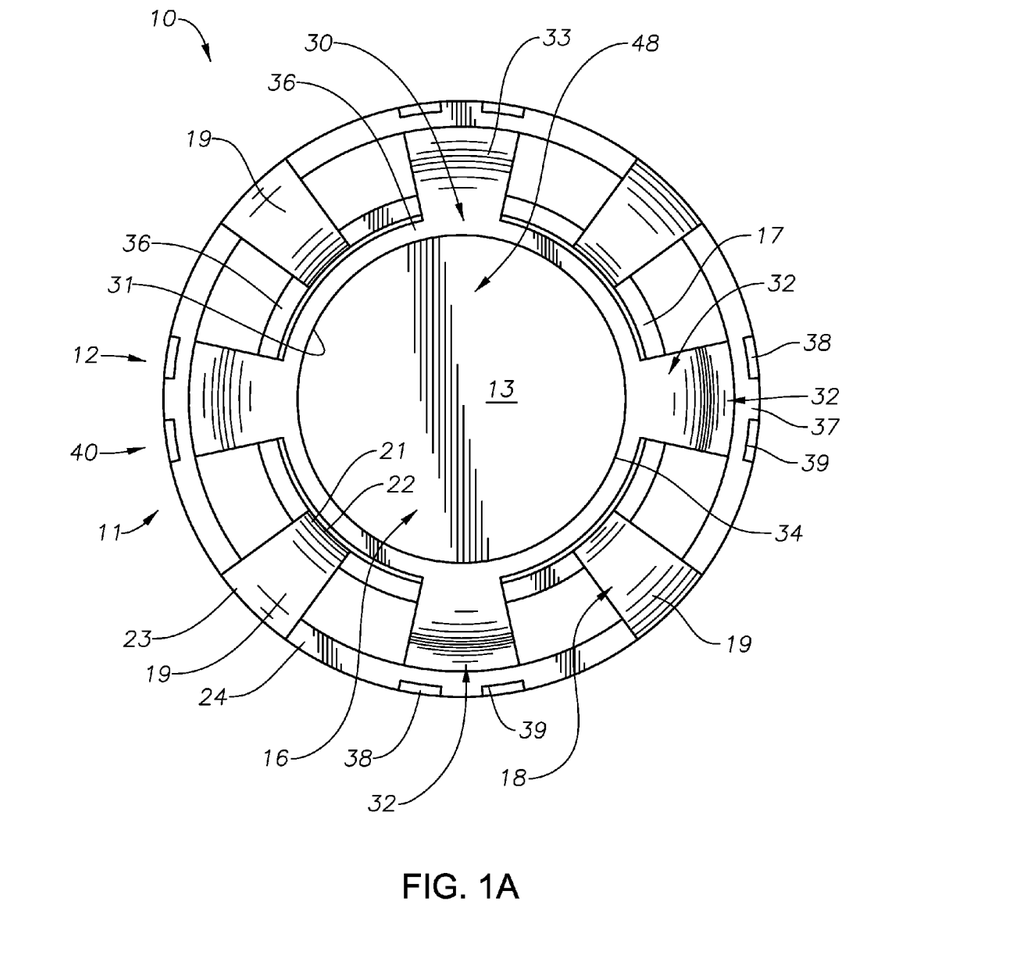
FIG. 1A is a plan view of one embodiment of a curvature changing accommodative IOL according to the principles of the present invention.
Figure 1B:
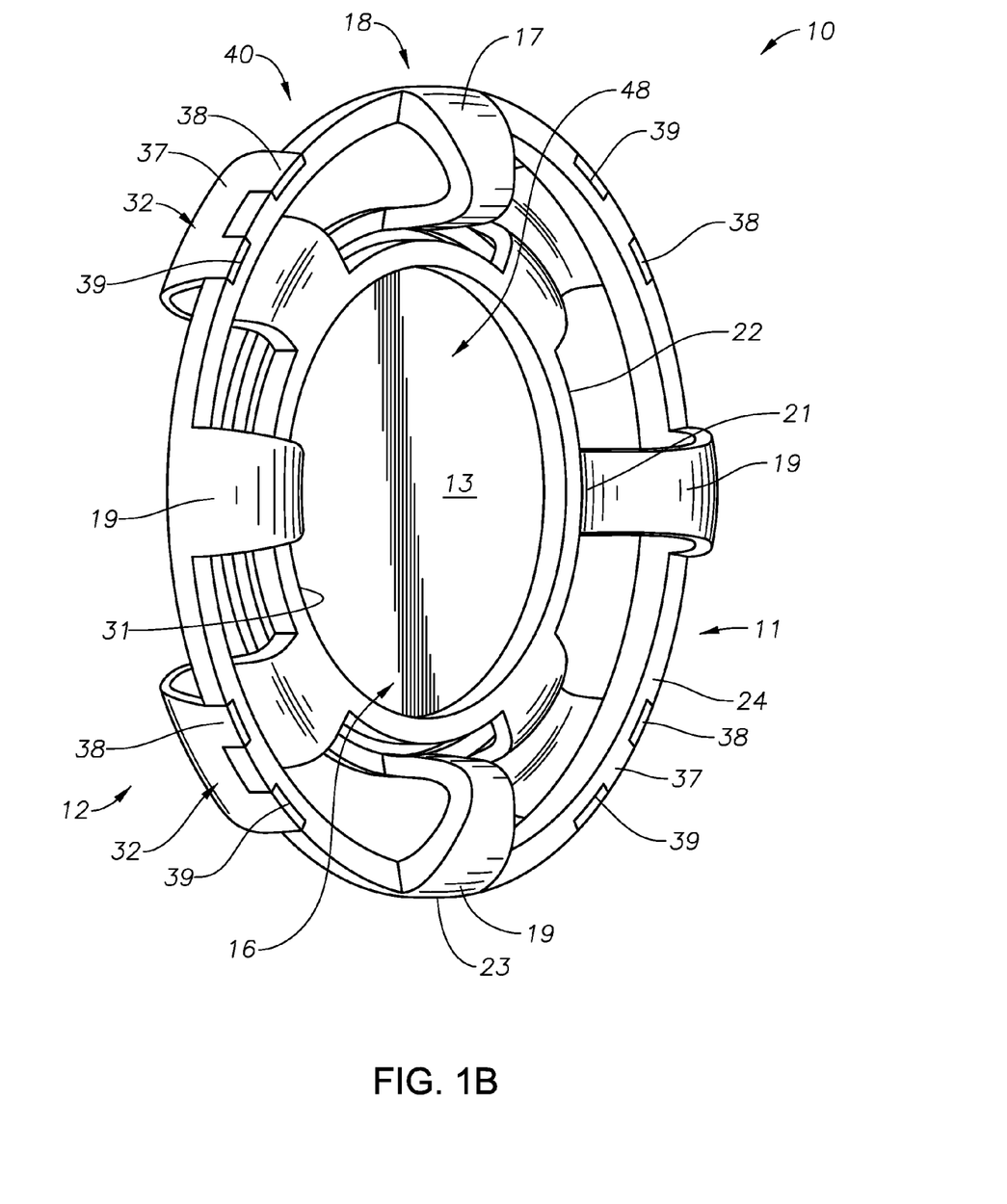
FIG. 1B is a perspective illustration of the embodiment of the curvature changing accommodating IOL illustrated in FIG. 1A.

As illustrated in FIGS. 1A and 1B, the IOL 10 generally includes a lens body 11 and an actuator 12 that engages and interfits with the lens body, with at least one fluidic optical element 13 being received therebetween so as to define a substantially unitary IOL structure. The lens body and actuator both can generally comprise a biocompatible material such as a flexible, resilient acrylic or silicone material. The fluidic optical element 13 can generally comprise a flexible membrane formed from a soft, flexible optic material such as an acrylic, silicone or hydrogel material, for example, being formed from an AcrySof® optic material as manufactured by Alcon Laboratories, Inc., and generally will be filled with a fluid material such as a liquid, gel or compressible solid material. The lens body 11 and actuator 12 can be locked or otherwise connected together in a substantially locked, friction fit type engagement, enabling detachment or disengagement for change-out of the fluidic optical element(s) therebetween, and/or further can be linked together in a substantially unitary structure by application of an adhesive or chemical bonding material, laser welding or plasma bonding, or other attachment methods as will be understood in the art. The IOL 10 also can be preassembled into a unitary, one-piece lens structure, as illustrated in FIGS. 1A and 1B, during manufacture, with one or more fluidic optical elements already installed between the actuator and lens body. Alternatively, it could be possible to provide for assembly of the actuator and lens body by the surgeon immediately prior to implantation into a patient's eye so that various fluidic optical elements having differing thicknesses (to greater provide varying degrees of accommodative amplitude) can be selected as needed to correct the patient's vision as closely as possible by the surgeon prior to implantation.

Figure 2A:
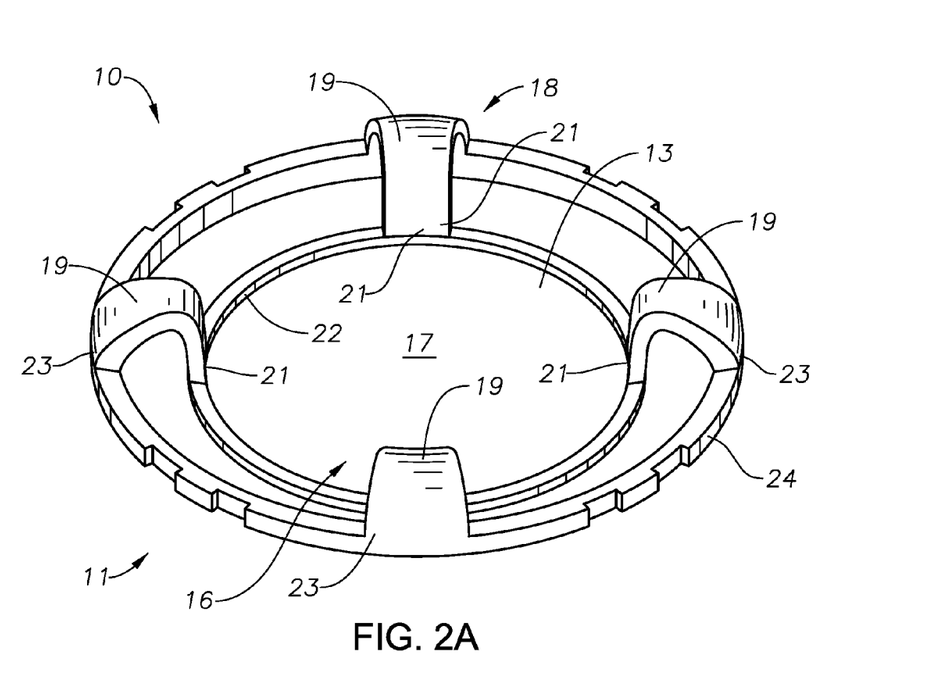
FIG. 2A is a perspective illustration of the base lens of the curvature changing accommodative IOL of FIGS. 1A-1B.

FIG. 2A generally illustrates one example embodiment of the lens body 11 of the curvature changing accommodative IOL 10 according to the principles of the present invention. As indicated in FIG. 2A, the lens body generally can comprise a substantially circular structure including a base lens 16 approximately centrally located therein and which base lens generally has a central portion having a base or predetermined curvature, as indicated at 17 in FIGS. 4A and 4B, so as to provide the base lens with a base optic power. This base optic power can be selected to provide a base line correction for adjusting the patient's distance vision and/or for correction of residual refractive errors or astigmatism of the patient's eye. The base lens generally will be formed from a soft, flexible lens material such as an acrylic, silicone or hydrogel material, and can be provided with a substantially fixed curvature so that the base optic power of the base lens generally can be maintained as substantially constant during accommodative operations of the patient's eye. However, it also will be understood that the base lens further could be designed to undergo some desired range of accommodative movement or curvature change, thus adjusting its optic power, as needed or desired.

The lens body 11 generally will include a haptic structure 18 including a series of curved, outwardly projecting lens haptic elements 19. While FIG. 2A illustrates the use of four lens haptic elements 19, it will be understood by those skilled in the art that a greater or lesser number of haptic elements also can be utilized within the haptic structure 18 of the lens body 11. Each of the lens haptic elements 19 will extend from a first or proximal end 21 formed or attached along an outer side edge 22 of the base lens 16 and will extend upwardly and outwardly to a second or distal end 23 spaced from the outer side edge 22 of the base lens 16. The haptic structure 18 further can include an outer peripheral connecting ring 24 that connects the second or distal ends 23 of the lens haptic elements 19 and helps provide further rigidity and a resilience to the haptic structure of the lens body. The lens haptic elements 19 and peripheral outer ring 24 further generally are formed from a more rigid material than the base lens so as to provide the haptic structure 18 (including the lens haptic elements 19 and outer peripheral ring 24) with an inherent resiliency and stiffness. As further indicated in FIGS. 2A and 3, the peripheral outer ring 24 of haptic structure 18 further is generally spaced from the peripheral side edge 22 of the base lens 16 so as to create a desired spacing to facilitate the interconnection of the actuator 12 therewith.

Figure 2B:
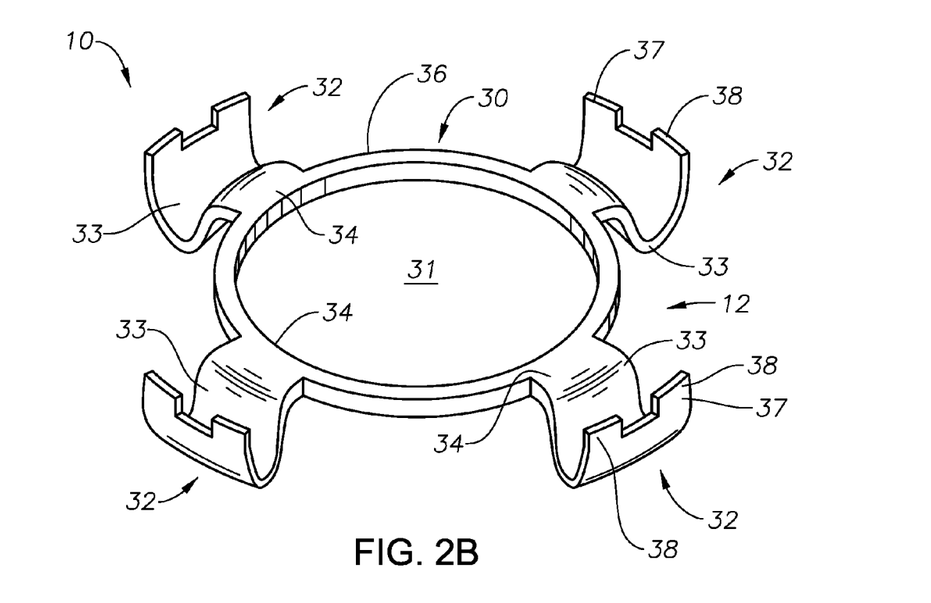
FIG. 2B is a perspective illustration of the actuator of the curvature changing accommodative IOL of FIGS. 1A-1B.
Figure 2C:
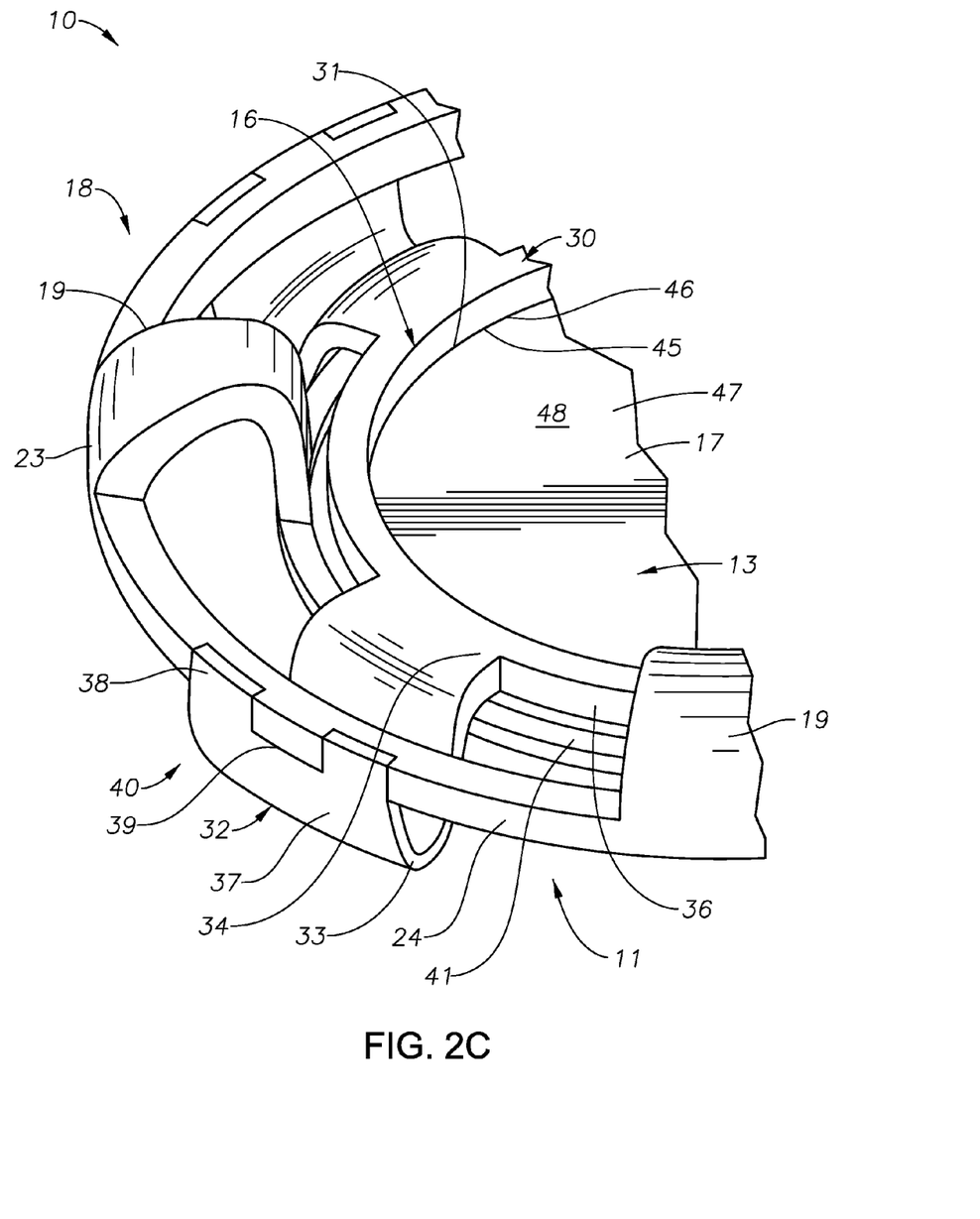
FIG. 2C is a perspective illustration showing the engagement of one of the actuator haptic elements with the haptic structure of the lens body as part of the cross-haptic structure of the curvature changing accommodative IOL.
Figure 3:
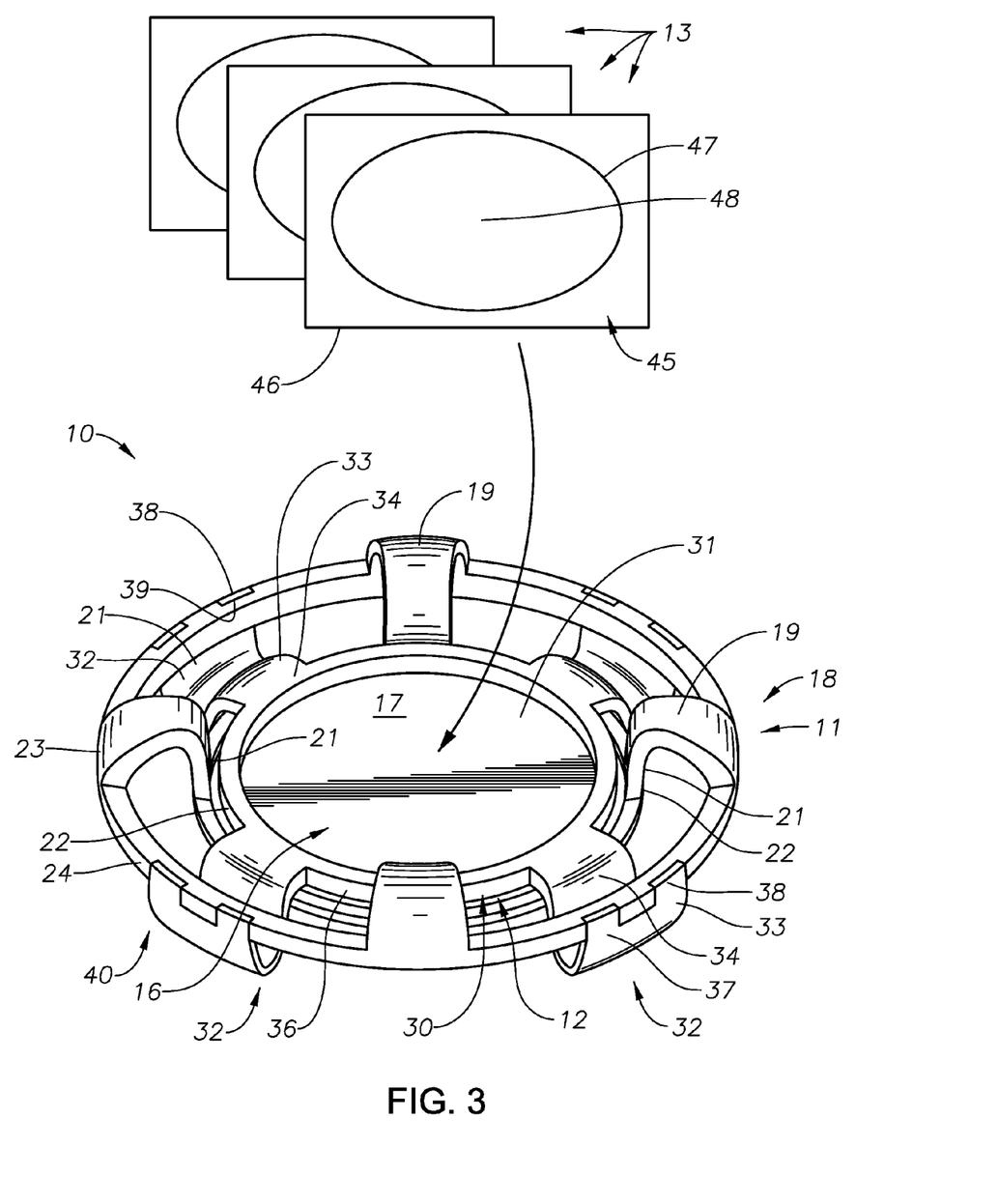
FIG. 3 is a perspective illustration illustrating the placement of one or more fluidic optical elements within the curvature changing accommodative IOL structure.
Figure 4A:
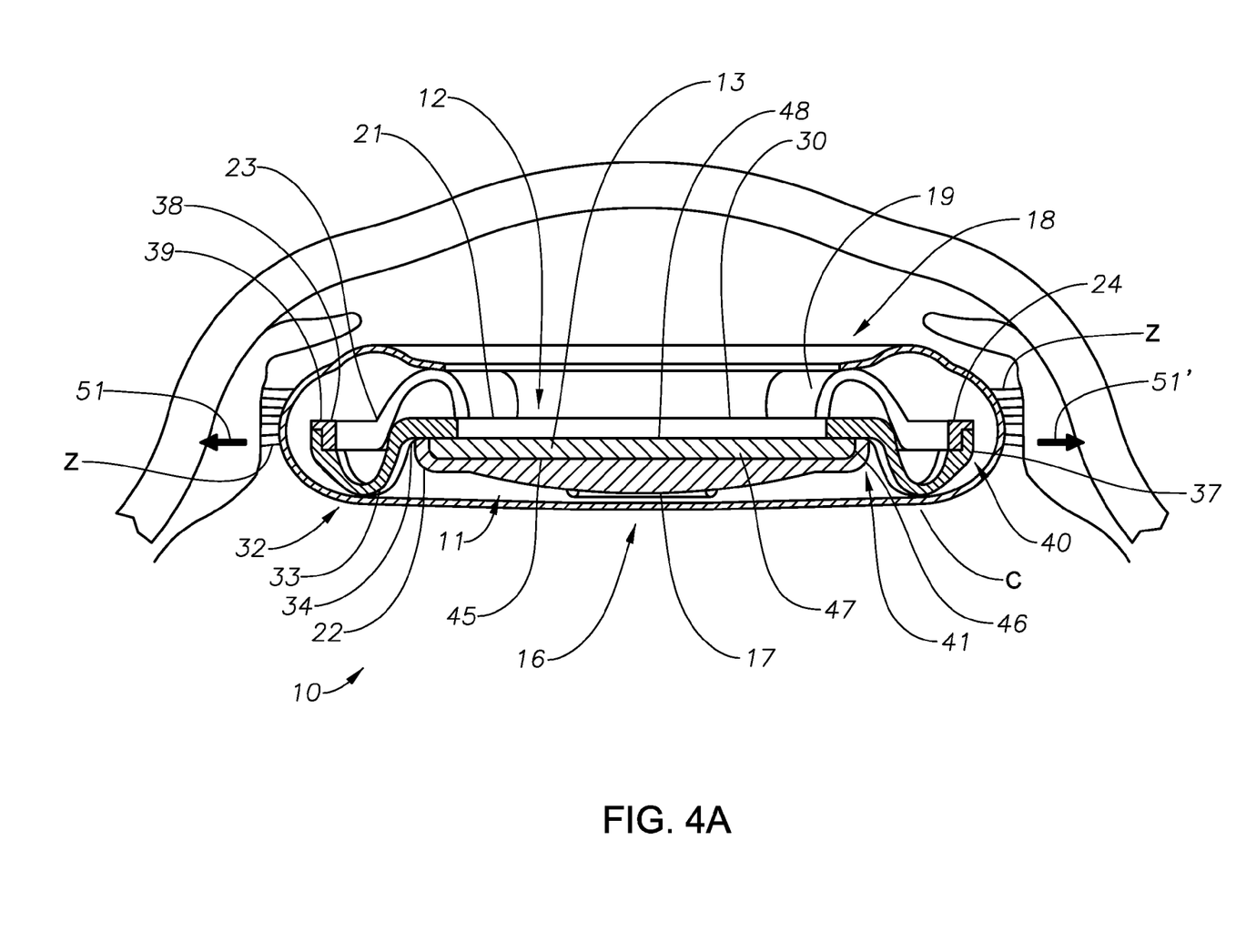
FIG. 4A is a cross-sectional view of the curvature changing accommodative IOL according to one embodiment, installed within the capsular bag of the patient's eye in its disaccommodated, at rest configuration.
Figure 4B:
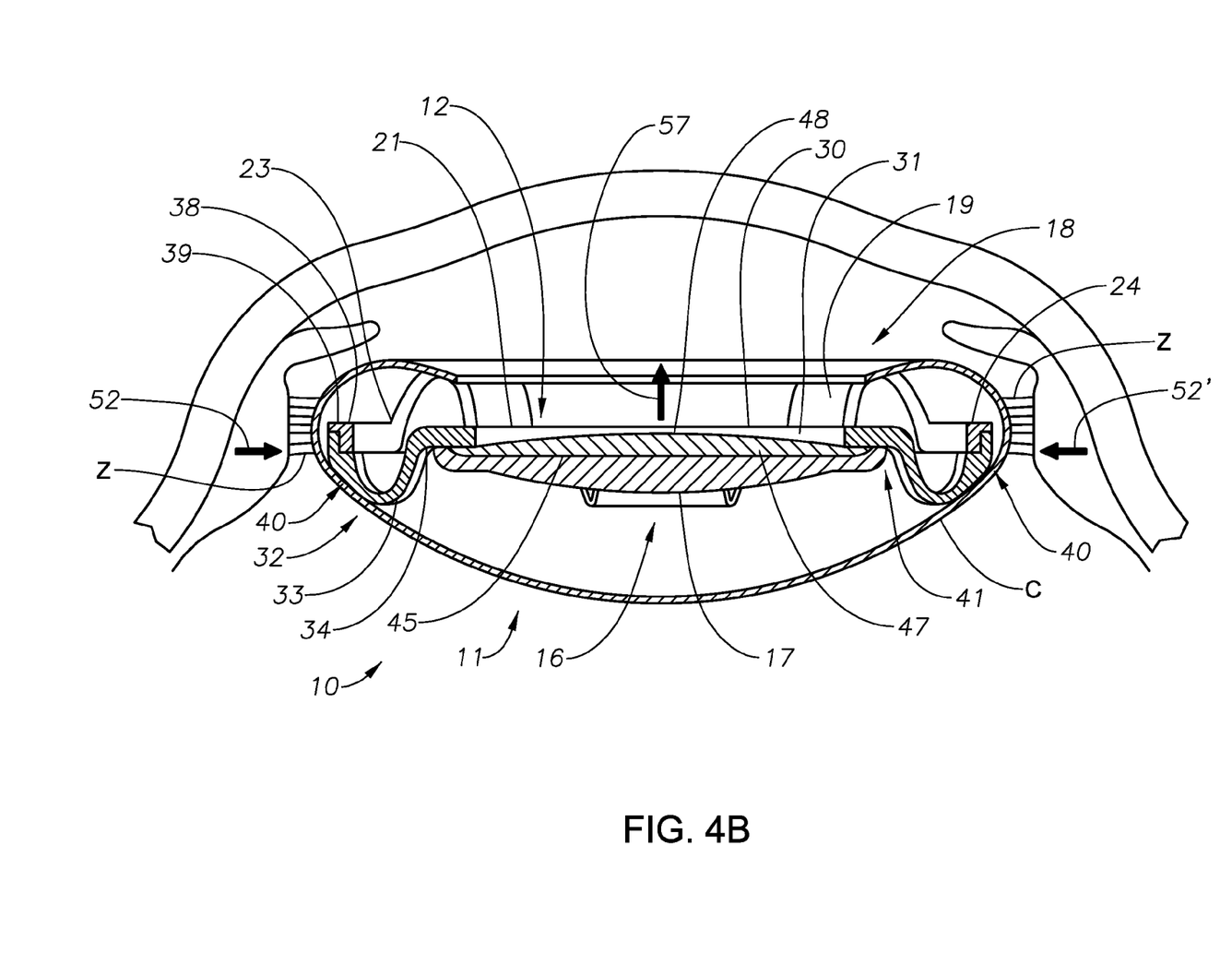
FIG. 4B is a cross-sectional view of the curvature changing accommodative IOL according to one embodiment, installed within the capsular bag of the patient's eye in its accommodated, compressed configuration.

As illustrated in FIGS. 1B, 2B and 3, the actuator 12 generally includes a substantially ring-shaped body 30, typically formed from a resilient biocompatible material such as an acrylic, silicone or hydrogel material, similar to the materials from which the lens body 11 can be formed. The actuator body 30 (FIG. 2B) defines a substantially circular, centrally located opening 31, which can be of a similar approximate size and configuration to the central portion 17 (FIG. 2A) of the base lens 16 such that when the actuator and lens body are installed together, as indicated in FIGS. 1A and 1B, the central opening 31 of the actuator body generally will be aligned with the central portion 17 of the base lens of the lens body.

As further indicated in FIGS. 2B and 3, the actuator 12 additionally includes a series of actuator haptic elements 32 that generally are formed with and project outwardly from the actuator body 30. While a series of four actuator haptic elements 32 are illustrated in the figures, it will be understood by those skilled in the art that greater or fewer actuator haptic elements also can be provided as needed or desired. Each of the actuator haptic elements 32 generally is shown as including an outwardly projecting and upwardly curved body portion 33 that extends from a first or proximal end 34 located along a peripheral side edge 36 of the actuator body and terminates at a distal or second end 37 having a series of hooked locking elements 38 formed therealong. As indicated in FIGS. 1A-1B and 3, the hooked locking elements 38 of the actuator haptic elements 32 generally are adapted to engage corresponding locking recesses 39 formed at spaced locations about the peripheral outer ring 24 of the haptic structure 18 of the lens body 11. As a result, the actuator can be locked into engagement with the lens body, with the locking elements of its actuator haptic elements engaging the peripheral outer ring of the haptic structure of the lens body in a snap-fit or frictional engagement.

The interconnection of the actuator with the lens body correspondingly creates a cross-haptic structure, indicated by numeral 40, as illustrated in FIGS. 1A-1B, 2C and 4A-5. This cross-haptic structure, whereby the actuator haptic elements 33 engage the outer peripheral ring 24 of the lens body haptic structure 18 creates a tensioned engagement between the base lens 16 of the lens body and the actuator body 30 so as to define an initial gap or spacing 41 (FIG. 4A) in which one or more fluidic optical elements 13 can be received in an initial, uncompressed state between the actuator body and the base lens of the lens body as indicated in FIG. 4A.

As illustrated in FIGS. 3-4B, each of the fluidic optical elements 13 generally can comprise a membrane or bag 45 of a flexible biocompatible material, which could include multiple layers or sheets typically sealed together about the edges 46 thereof. An aqueous fluid material 47, such as a liquid, gel or compressible solid material utilized for optics applications, will be received within and fill the membrane 45 of the fluidic optical element. The fluid material 47 will fill the interior of the membrane, providing the membrane with a desired thickness when in a flattened, disengaged condition wherein the fluidic optical element generally is provided with a minimal or null/zero optic power when the fluidic optic element is in a normal, uncompressed or at rest state. The thickness of the fluidic optical element generally can correspond to a measured thickness of the gap 41 defined between the actuator body and the base lens of the lens body such that when the fluidic optical element is received between the actuator and lens body, it can remain in a substantially uncompressed, flattened condition or state, providing minimal or substantially no optic power to the accommodating IOL 10 in addition to the predetermined base optic power of the base lens thereof.

Alternatively, as indicated in FIG. 3, it further is possible to include multiple fluidic optical elements that can be placed in a stacked array between the base lens and actuator body. Such stacked fluidic optic elements also can be of varying thicknesses and which can have different fluid materials therein to provide different compression rates to further vary or adjust the power of the base lens prior to and/or during an accommodative movement of the patient's eye. Still further, the fluidic optic element of multiple elements when used, can be removable/replaceable elements of the IOL. For example, if it is determined that the patient's distance vision has deteriorated over time, additional or substitute fluidic optical elements which have a desired optic power when in their normal, uncompressed state can be inserted into the IOL 10, either as a replacement or substitute for the existing fluidic optical element(s) or in addition to one or more installed fluidic optical elements to thus provide further optic power in addition to the base optic power of the base lens for correcting additional deficiencies in the patient's distance vision without requiring accommodation of the patient's eye.

In use of the accommodating IOL 10 according to the present invention, as illustrated in FIGS. 4A and 4B, the accommodating IOL 10 generally can be preassembled prior to implantation into the capsular bag C of a patient's eye. To assemble the accommodating IOL, a lens body having a base lens with a desired base optic power for correcting certain visual deficiencies of the patient's eye, for example, for replacement of a natural crystalline lens that has become clouded with cataracts, and/or to correct residual refractive errors and astigmatism. Thereafter, one or more fluidic optical elements 13 will be applied to the base lens, with a center portion 48 of such fluidic optical element(s) generally being substantially located or aligned in front of the base lens. Thereafter, the actuator 12 will be installed into locked engagement with the lens body by inserting the actuator haptic elements 32 beneath and around the peripheral outer ring 24 of the lens body, with the locking elements of the actuator haptic elements engaging the locking recesses of the outer peripheral ring of the lens body haptic structure in a tight, tensioned engagement. As a result of such a tensioned arrangement, the outwardly and downwardly curved lens haptic elements 19 of the lens body haptic structure 18 will tend to apply a downwardly biasing force against the outer or distal ends of the actuator haptic elements, which will tend to create the separation or gap 41 in which the fluidic optical element(s) 13 is positioned as indicated in FIG. 4A.

Figure 5:
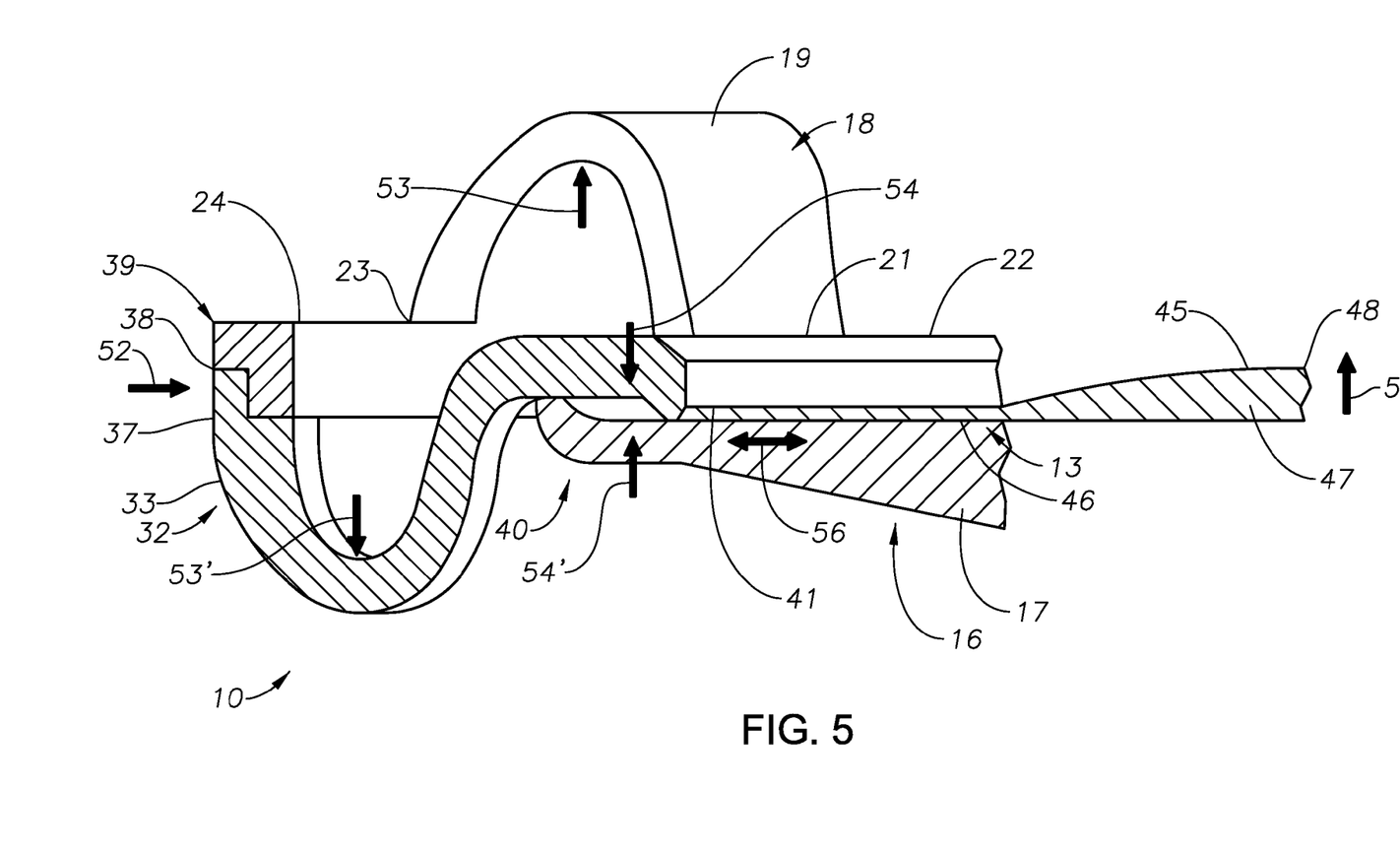
FIG. 5 is a schematic illustration of the cross-haptic structure of the curvature changing accommodative IOL, illustrating the different forces being applied during accommodation and disaccommodation operations of the patient's eye.

The assembled accommodative IOL 10 thereafter will be implanted into a patient's eye, with the IOL 10 generally being inserted into the capsular bag C of the patient's eye through a capsular-hexis. The IOL generally will be inserted into the capsular bag as a replacement for the natural crystalline lens of the patient's eye, with the cross-haptic structure 40 defined by the engagement of the haptic structure 18 of the lens body and the actuator haptic elements 32 generally engaging inside surfaces of the capsular bag as indicated in FIG. 4A. After implantation, when the patient's eye is in a disaccommodated or unaccommodated state, the ciliary muscles of the patient's eye will generally relax, causing the zonules Z connecting the capsular bag to the ciliary muscles of the eye to exert a pulling or tension force on the capsular bag, indicated by arrows 51/51' in FIG. 4A. This tension force will tend to pull the capsular bag outwardly, causing some compression of the capsular bag, which in turn exerts a compressive force on the actuator haptic elements and the haptic elements of the lens body haptic structure. As a result, the opposed haptic elements tend to be urged into tighter engagement against one another as shown in FIGS. 4A and 5, so as to maintain the gap 41 between the actuator and lens body, thus generally leaving the fluidic optical element in an uncompressed, substantially flattened state. In such a disaccommodated state or configuration, the base lens provides the primary optic power for correction of the patient's distance vision, with no additional optical power generally being needed.

As indicated in FIG. 4B, during an accommodating movement or operation of the patient's eye, the ciliary muscles of the patient's eye will tend to expand inwardly and forwardly. The expansion of the ciliary muscles will tend to release the bag causing forces, indicated by arrows 52/52' in FIG. 4B, to be produced in the cross-haptic structure 40 of the IOL 10. As a result, as indicated in FIG. 5, the outer or distal ends of each of the lens haptic elements and actuator haptic elements generally will be urged away from each other in the direction of arrows 53 and 53'. This in turn will cause the proximal ends or portions of the actuator haptic elements and the lens body haptic elements to be urged toward each other and toward engagement with the fluidic optical element, as indicated by arrows 54 and 54'.

The proximal ends of these haptic elements accordingly will exert an axial compressive force against the fluidic optical element 13, causing the fluid material 47 of the fluidic optical element 13 to be urged inwardly in the direction of arrow 56 toward the center portion 48 of the fluidic optical element. The compression of the fluid material and movement thereof toward the center portion of the fluidic optical element and away from its side edges, which are generally captured and being squeezed or compressed between the base lens and actuator body, causes the center portion of the fluidic optical element to bulge outwardly and/or forwardly, as indicated by arrow 57 in FIGS. 4B and 5, changing its curvature and generating further optic power for the accommodating IOL in addition to the base optic power of the base lens. The cross-haptic connection between the actuator body and the base lens of the lens body further creates a ring pressure when subjected to compression due to an accommodating movement of the ciliary muscles. As a result, the axial compressive force being applied to the fluid material within the fluidic optical element is substantially equalized about the circumference thereof. This helps provide a controlled and substantially even change of the curvature of the fluidic optical element to increase and add additional optic power to the IOL to help the patient focus on nearer or closer objects in response to the natural accommodative operation or movement of the patient's eye.

When the patient's eye undergoes a disaccommodative movement, so as to return to an unaccommodated, relaxed or at rest state, the ciliary muscles again will relax, so that the axial compressive force being applied by the engagement of the cross-haptic structure of the lens haptic elements and actuator haptic elements to dissipate. Thereafter, as the zonules (FIG. 4A) are stretched with the further relaxing of the ciliary muscles of the patient's eye, the haptic elements will again be subjected to compressive forces as acting on upper and lower surfaces thereof so as to increase/return the gap between the actuator body and the base lens of the lens body. With this gap reestablished, the fluid material within the fluidic optical element is permitted to flow outwardly toward the side edges thereof and thus return the fluidic optical element to its native, uncompressed state reducing the additional optic power being provided thereby and enabling the patient's eye to refocus on more distant objects.

The accommodative IOL of the present invention thus provides a means for changing the curvature of the IOL in response to the natural accommodative movement of the patient's eye, to enable consistent, continued accommodation of the patient's vision from far to near objects with an accommodative amplitude of greater than two diopters, while minimizing or substantially eliminating the effects of unknown capsular bag and capsulorhexis sizes, and further enabling replacement or adjustment of appropriate fluidic optical elements to provide future vision corrections as needed. In addition, the cross-haptic structure provided by the accommodative IOL of the present invention utilizes axial compressive forces working in opposite directions for disaccommodative and accommodative states of the patient's eye to thus provide a strong axial reaction force of upwards of 3 mN or greater so as to minimize the effects of fibrosis or the thickening of the patient's capsular bag over time. Still further, the accommodative IOL also enables adjustment and/or correction of further vision deficiencies, even over time, by the replacement and/or addition of the fluidic optical elements, as well as enabling a selectable and easily reconfigurable IOL configuration that allows the use of the present IOL in accommodative, monofocal or multifocal IOL implantations, with or without astigmatism correction. The implantation of the accommodative IOL of the present invention within the capsular bag, with the non-contact of the base lens and fluidic optical element to the anterior and posterior portions of the capsular bag also can help promote circulation of the aqueous humor within the capsular bag to additionally help minimize collection and proliferation of epithelial cells and the formation of posterior capsular opacification (PCO), which can lead to clouding of the lens akin to cataracts.

The foregoing description generally illustrates and describes various embodiments of the present invention. It will, however, be understood by those skilled in the art that various changes and modifications can be made to the above-discussed construction of the present invention without departing from the spirit and scope of the invention as disclosed herein, and that it is intended that all matter contained in the above description or shown in the accompanying drawings shall be interpreted as being illustrative, and not to be taken in a limiting sense. Furthermore the scope of the present disclosure shall be construed to cover various modifications, combinations, additions, alterations, etc. above and to the above-described embodiments, which shall be considered to be within the scope of the present invention. Accordingly, various features and characteristics of the present invention as discussed herein may be selectively interchanged and applied to other illustrated and non-illustrated embodiments of the invention.

The invention claimed is:

1. An accommodative intraocular lens (IOL), comprising:
a lens body having a substantially circular base lens with a base optic power for providing a base vision correction and a haptic structure connected to a peripheral side edge of the base lens, wherein the haptic structure of the lens body comprises a peripheral outer ring spaced from the base lens and a series of curved, outwardly projecting lens haptic elements extending between and connecting the peripheral outer ring of the haptic structure and the peripheral edge of the base lens;
an actuator mountable over the base lens of the lens body, the actuator comprising a ring-shaped body defining a substantially circular, centrally located opening and a series of radially projecting actuator haptic elements adapted to engage and attach the actuator to the lens body to form a substantially unitary structure, the centrally located opening of the actuator aligned with and seated upon the peripheral edge of the base lens, and initially arranged in a spaced position with respect to the base lens so as to define a measured gap therebetween; and a fluidic optical element received within the gap between the base lens of the lens body and the actuator without being attached to the lens body or the actuator in an initial substantially flattened uncompressed state, the fluidic optical element comprising a flexible membrane including a fluid material contained therein, and having a size and shape corresponding to said measured gap;

wherein the interconnection of the actuator with the lens body creates a cross-haptic structure, wherein once installed in a patient's eye, as the patient's eye undergoes accommodation, the actuator and lens body are urged inwardly, generating a ring pressure that acts on the fluidic optical element, causing movement of the fluid material therein and deformation of the fluidic optical element so as to provide a further optical power in addition to the base optic power of the base lens, wherein as the patient's eye undergoes a disaccommodative movement, a tension force is applied to at least one of the lens haptic elements or the actuator haptic elements, causing a separation of the lens haptic elements and actuator haptic elements so as to dissipate the force applied to the fluidic optical element, enabling the fluidic optical element to return to said substantially flattened uncompressed state and reduce the optical power of the intraocular lens.

2. The accommodative intraocular lens of claim 1, wherein the lens body and actuator are chemically bonded together.

3. The accommodative intraocular lens of claim 1, wherein the lens body and the actuator are welded together.

* * * * *